(12) United States Patent
Stallworth

(10) Patent No.: US 12,370,076 B2
(45) Date of Patent: Jul. 29, 2025

(54) HARPER PEAR CUSHION

(71) Applicant: Rachel Harper Stallworth, Crestview, FL (US)

(72) Inventor: Rachel Harper Stallworth, Crestview, FL (US)

(\*) Notice: Subject to any disclaimer, the term of this patent is extended or adjusted under 35 U.S.C. 154(b) by 0 days.

(21) Appl. No.: 17/402,509

(22) Filed: Aug. 14, 2021

(65) Prior Publication Data

US 2023/0045903 A1  Feb. 16, 2023

(51) Int. Cl.
*A61F 6/08* (2006.01)
*A61F 6/14* (2006.01)

(52) U.S. Cl.
CPC . *A61F 6/08* (2013.01); *A61F 6/14* (2013.01)

(58) Field of Classification Search
CPC .................................. A61F 6/08; A61F 6/14
See application file for complete search history.

(56) References Cited

U.S. PATENT DOCUMENTS

| | | | | |
|---|---|---|---|---|
| 2005/0203399 | A1* | 9/2005 | Vaezy | A61B 8/0833 600/439 |
| 2008/0047563 | A1* | 2/2008 | Tal | A61F 6/18 128/831 |
| 2011/0226258 | A1* | 9/2011 | Black | A61F 2/0004 128/834 |
| 2013/0138135 | A1* | 5/2013 | Rosen | A61B 17/12 606/197 |
| 2015/0351886 | A1* | 12/2015 | Carey | A61B 17/12136 606/193 |
| 2016/0008215 | A1* | 1/2016 | Pfeiffer | A61H 23/02 600/38 |
| 2017/0301263 | A1* | 10/2017 | Souter | G09B 23/30 |

FOREIGN PATENT DOCUMENTS

WO    WO 2014/059432 A3 *  4/2014

* cited by examiner

*Primary Examiner* — Camtu T Nguyen
(74) *Attorney, Agent, or Firm* — Ronald Baker, Esq.; BAKER & Co. LAW

(57) ABSTRACT

Disclosed is a medical device for use during sexual intercourse for a female who has underwent a hysterectomy. The medical device includes a flexible body and a ring for insertion and removal. The device is utilized to relieve lower back and leg pain during a performance of sexual intercourse.

7 Claims, 2 Drawing Sheets

HARPER PEAR CUSHION

TECHNICAL FIELD

The presently disclosed embodiments are related, in general, to a female medical device. More particularly, the presently disclosed embodiment is related to the medical device that acts as a cushion to alleviate low back and leg pain during intimacy among couples. The device will act as an artificial uterus in essence to provide a feeling of a uterus during sexual encounters.

BACKGROUND

The subject matter discussed in the background section should not be assumed to be prior art merely as a result of its mention in the background section. Similarly, a problem mentioned in the background section or associated with the subject matter of the background section should not be assumed to have been previously recognized in the prior art. The subject matter in the background section merely represents different approaches, which in-and-of-themselves may also be inventions.

Typically, women encounter a hysterectomy for a number of reasons that can be a painful ordeal both physically and emotionally. To further elaborate, this experience can be a difficult recovery and often can affect intimacy between couples due to absence of certain sensations during sexual encounters. The absence of the uterus can decrease the sexual experience for a male due to the lack of physical sensation that a uterus would otherwise provide. Prior art presents female solutions such as US2015/0257925 issued to Schwartz, discloses a gel-based seals and fixation device for preventing pregnancy. The device includes an intrauterine device that can be inserted into the uterine cavity for such purposes that is composed of a silicone, rubber or similar material that is safe for the body.

However, the existing medical devices are not user-friendly and primarily utilized for contraceptive purposes. Therefore, there is a necessity for a medical device that can be used in a manner that will allow a user to discretely apply and remove without much discomfort.

Thus, in view of the above, there is a long-felt need in the medical industry to address the aforementioned deficiencies and inadequacies.

Further limitations and disadvantages of conventional and traditional approaches will become apparent to one of skill in the art, through comparison of described devices with some aspects of the present disclosure, as set forth in the remainder of the present application and with reference to the drawings.

SUMMARY

According to the embodiment illustrated herein, there may be provided a female medical device for user's who have underwent a hysterectomy and desire to maintain intimacy. The device includes a pharmaceutical product that is made of silicone or similar material. The device is configured to promote a satisfying sexual experience between couples. The embodiment includes a pear-shaped body with a ring for inserting and removing the device from a woman's uterine cavity. The embodiment is a cavity-conforming material that is shaped to fit a uterus of a female human and primarily fits into the uterine cavity for increased comfort once inserted into the cavity area. The device is sized to fit the uterus cavity which is typically 2 by 2.5 inches.

A further embodiment provides a method for inserting a human female medical device through the vaginal canal. A pear-shaped device sized to fit a uterus is held by a user's finger via the ring and inserted into the vagina until securely in the uterine cavity. The device is removed by placing a user's finger in the ring and pulled through the vaginal cavity to extract the device. The device can be easily cleaned using antibacterial soap and warm water.

These and other features and advantages of the present disclosure may be appreciated from a review of the following detailed description of the present disclosure, along with the accompanying figures in which reference numerals refer to like parts throughout.

BRIEF DESCRIPTION OF DRAWINGS

The accompanying drawings illustrate the various embodiments of systems, methods, and other aspects of the disclosure. Any person with ordinary skills in the art will appreciate that the illustrated element boundaries (e.g., boxes, groups of boxes, or other shapes) in the figures represent one example of the boundaries. In some examples, one element may be designed as multiple elements, or multiple elements may be designed as one element. In some examples, an element shown as an internal component of one element may be implemented as an external component in another and vice versa. Further, the elements may not be drawn to scale.

Various embodiments will hereinafter be described in accordance with the appended drawings, which are provided to illustrate and not to limit the scope in any manner, wherein similar designations denote similar elements, and in which.

DETAILED DESCRIPTION

The present disclosure may be best understood with reference to the detailed figures and description set forth herein. Various embodiments are discussed below with reference to the figures. However, those skilled in the art will readily appreciate that the detailed descriptions given herein with respect to the figures are simply for explanatory purposes as the device and method may extend beyond the described embodiments. For example, the teachings presented and the needs of a particular application may yield multiple alternative and suitable approaches to implement the functionality of any detail described herein. Therefore, any approach may extend beyond the particular implementation choices in the following embodiments described and shown.

References to "one embodiment," "at least one embodiment," "an embodiment," "one example," "an example," "for example," and so on indicate that the embodiment(s) or example(s) may include a particular feature, structure, characteristic, property, element, or limitation but that not every embodiment or example necessarily includes that particular feature, structure, characteristic, property, element, or limitation. Further, repeated use of the phrase "in an embodiment" does not necessarily refer to the same embodiment.

The terms "a" or "an", as used herein, are defined as one, or more than one. The term "plurality", as used herein, is defined as two, or more than two. The term "another", as used herein, is defined as at least a second or more. The terms "including" and/or "having", as used herein, are defined as comprising (i.e., open language). The term "coupled", as used herein, is defined as connected, although not necessarily directly, and not necessarily mechanically.

Headings of sections provided in this patent application and the title of this patent application are for convenience only and are not to be taken as limiting the disclosure in any way. A description of an embodiment with several components in connection with each other does not imply that all such components are required.

Figure 1:
FIG. 1 is a perspective view of the Harper Pear Cushion for use during sexual contact, in accordance with at least one embodiment.

FIG. 1 is a perspective view of a medical device (100) for maintaining intimacy of couples when engaged in sexual intercourse, in accordance with at least one embodiment. The medical device (100) includes a ring (102), and a filler end (104) that occupies space within the uterine cavity (202). The filler end (104), is configured to have an average size range from 2 to 2.5 inches. The ring (102) and the filler end (104) make up what is referred to as a flexible member. The flexible member is ideally the total body of the embodiment that is inserted into the uterine cavity (202). In an embodiment, the medical device (100) is held by a user's finger inserted into the ring (102) and subsequently inserted into the female's vagina with the filler end (104) being inserted first until the medical device (100) is fully seated in the uterine cavity (202). This process is revered when the female removes the medical device (100) by utilizing a finger to be engaged into the ring (102) and carefully removed from the uterine cavity (202) through the vagina. In a non-limiting example, the device can be made of silicone or similar material that is non in the art.

Figure 2:
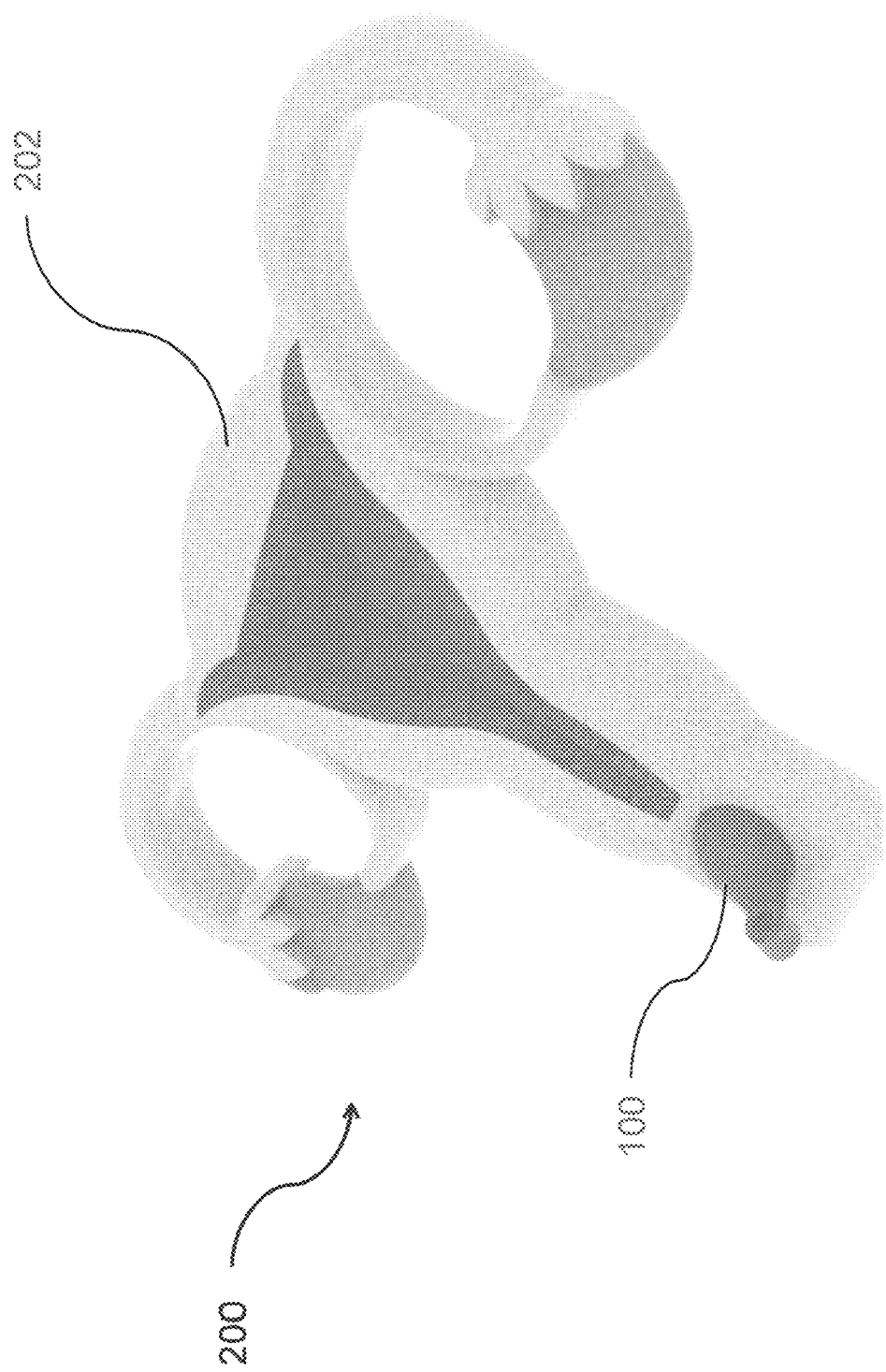
FIG. 2 is a perspective view of the female reproductive organs, in accordance with at least one embodiment.

FIG. 2 is a perspective view of a female reproductive organs, in accordance with at least one embodiment. In an embodiment, the female reproductive organs (200) include the uterine cavity (202). In an embodiment, the medical device (100) is depicted being inserted into a female's vaginal area with the filler end (104) shown being inserted first. The absence of the uterus can decrease the sexual experience for a male due to the lack of physical sensation that a uterus would otherwise provide. One of the primary purposes of the embodiment is to provide a sensation of a naturally developed uterus for the male during those times of sexual intercourse. Furthermore, the medical device (100) is utilized to relieve lower back and leg pain during sexual intercourse which can be an ordeal for those who have underwent a hysterectomy. The filler end (104) is filled with a silicone gel.

A person skilled in the art will understand that the medical device is described herein for illustrative purposes and should not be construed to limit the scope of the disclosure.

A person with ordinary skills in the art will appreciate that the device has been illustrated and explained to serve as examples and should not be considered limiting in any manner. It will be further appreciated that the variants of the above-disclosed features and functions, or alternatives thereof, may be combined to create other different apparatuses or applications.

While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

What is claimed is:

1. A medical device, comprising:
   a flexible member for removably inserting into a uterine cavity, wherein the flexible member comprising:
   a ring end to facilitate a user to remove the flexible member from the uterine cavity; and
   a filler end adapted to be inserted into the uterine cavity;
   wherein the filler end is adapted to occupy space within the uterine cavity;
   wherein the flexible member is adapted to be removed from the uterine cavity by engaging a finger of the user into the ring end and removing the filler end from the uterine cavity through the vagina;
   wherein the filler end is filled with a silicone gel, wherein the filler end is configured to have an average size range from 2 to 2.5 inches; and
   wherein the flexible member is adapted to be inserted into the uterine cavity and being kept within the uterine cavity so as to provide increased sexual sensation during a performance of sexual intercourse.

2. The medical device as claimed in claim 1, wherein the filler end comprises an outer layer and an inner and defining a gap therebetween, wherein the gap is filled with the silicon gel.

3. The medical device as claimed in claim 1, wherein the flexible member is made of soft silicone.

4. The medical device as claimed in claim 1 is a unitary device.

5. The medical device as claimed in claim 1, wherein the filler end is a pear-shaped body.

6. The medical device as claimed in claim 1, wherein the flexible member adapted to remain inserted within the uterine cavity for about 8 hours.

7. The medical device as claimed in claim 1, wherein the filler end is adapted to prevent lower back and leg pain during the performance of sexual intercourse.

* * * * *